United States Patent [19]

Schneider

[11] 4,102,897

[45] Jul. 25, 1978

[54] DIALKYLACETAL-CONTAINING THROMBOXANE B, 1,9-LACTONE INTERMEDIATES

[75] Inventor: William P. Schneider, Kalamazoo, Mich.

[73] Assignee: The Upjohn Company, Kalamazoo, Mich.

[21] Appl. No.: 830,538

[22] Filed: Sep. 6, 1977

Related U.S. Application Data

[60] Division of Ser. No. 716,473, Aug. 20, 1976, Pat. No. 4,070,384, which is a continuation-in-part of Ser. No. 676,894, Apr. 14, 1976, Pat. No. 4,018,804.

[51] Int. Cl.² ........................................... C07D 313/00
[52] U.S. Cl. .................................... 260/343; 542/413; 542/441
[58] Field of Search ................. 260/343; 542/413, 441

[56] References Cited

U.S. PATENT DOCUMENTS 4,049,648  9/1977  Bundy ........................... 260/343.41

*Primary Examiner*—Natalie Trousof
*Assistant Examiner*—Jane T. Fan
*Attorney, Agent, or Firm*—Robert A. Armitage

[57] ABSTRACT

The present specification provides novel intermediates and novel processes for the synthesis of various side chain and skeletal analogs of Thromboxane $B_2$ ($11\beta$-homo-11a-oxa-$PGF_{2\alpha}$). These analogs are particularly and especially useful as reproductive cycle control agents.

2 Claims, No Drawings

DIALKYLACETAL-CONTAINING THROMBOXANE B, 1,9-LACTONE INTERMEDIATES

CROSS REFERENCE TO RELATED APPLICATION

The present application is a divisional application of Ser. No. 716,473, filed Aug. 20, 1976, now issued as U.S. Pat. No. 4,070,384; which is a continuation-in-part of Ser. No. 676,894, filed Apr. 14, 1976, issued as U.S. Pat. No. 4,018,804 on Apr. 19, 1977.

The present invention relates to processes and intermediates for Thromboxane B compounds for which the essential material constituting a disclosure therefor is incorporated by reference herein from U.S. Pat. No. 4,020,173, issued Apr. 26, 1977 and U.S. Pat. No. 4,070,384, issued Jan. 24, 1978. One species of the present invention is (8S,9R,12S)-8[(1'S)-3'-oxo-1'-hydroxypropyl]-9,12-dihydroxy-cis-5-trans-10-heptadecadienoic acid, 9,12 diacetate, dimethylacetal, 1,1'-lactone.

I claim:
1. A thromboxane intermediate of the formula:

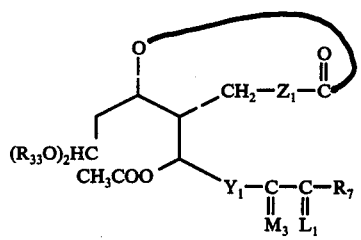

wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—, (7) 

(8) 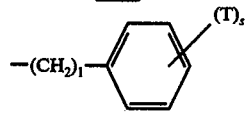

wherein $g$ is one, 2, or 3;
wherein $Y_1$ is trans-CH=CH- or -CH$_2$-CH$_2$-;
wherein $M_3$ is

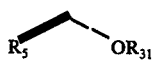

-continued
or

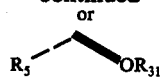

wherein $R_5$ is hydrogen or methyl and $R_{31}$ is a hydroxyhydrogen replacing group; wherein $L_1$ is

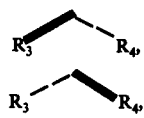

or a mixture of

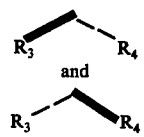

wherein $R_3$ and $R_4$ are hydrogen, methyl, or fluoro, being the same or different with the proviso that one of $R_3$ and $R_4$ is methyl only when the other is hydrogen or methyl; and
wherein $R_7$ is
(1) —(CH$_2$)$_m$—CH$_3$, (2) $-O-\underset{(T)_s}{\text{phenyl}}$, or (3) $-(CH_2)_l-\underset{(T)_s}{\text{phenyl}}$ wherein $l$ is zero, one, two, or three, where $m$ is one to 5, inclusive, T is alkyl of one to 3 carbon atoms, inclusive, alkoxy of one to 3 carbon atoms, inclusive, chloro, fluoro, or trifluoromethyl, and s is one, two, or 3, the various T's being the same or different, with the proviso that not more than two T's are other than alkyl, with the further proviso that $R_7$ is

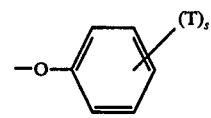

only when $R_3$ and $R_4$ are hydrogen or methyl, being the same or different; and
wherein $R_{33}$ is alkyl of one to 5 carbon atoms inclusive.

2. (8S,9R,12S)-8[(1'S)-3'-oxo-1'-hydroxypropyl]-9,12-dihydroxy-cis-5-trans-10-heptadecadienoic acid, 9,12-diacetate, dimethylacetal, 1,1'-lactone, a thromboxane intermediate according to claim 1.

* * * * *